United States Patent
West et al.

(10) Patent No.: US 9,778,248 B2
(45) Date of Patent: Oct. 3, 2017

(54) METHOD FOR MEASUREMENT OF THROMBOCYTE FUNCTION

(71) Applicant: Leibniz—Institut fuer Analytische Wissenschaften—ISAS—e.V., Dortmund (DE)

(72) Inventors: Jonathan West, Southampton (GB); Dirk Janasek, Dortmund (DE); Albert Sickmann, Dortmund (DE)

(73) Assignee: Leibniz—Institut fuer Analytische Wissenschaften—ISAS—e.V., Dortmund (DE)

( * ) Notice: Subject to any disclaimer, the term of this patent is extended or adjusted under 35 U.S.C. 154(b) by 0 days.

(21) Appl. No.: 14/835,834

(22) Filed: Aug. 26, 2015

(65) Prior Publication Data

US 2016/0061819 A1   Mar. 3, 2016

(30) Foreign Application Priority Data

Aug. 27, 2014 (DE) .................. 10 2014 112 270

(51) Int. Cl.
| | | |
|---|---|---|
| *G01N 33/50* | (2006.01) | |
| *G01N 15/10* | (2006.01) | |
| *G01N 33/49* | (2006.01) | |
| *G01N 27/447* | (2006.01) | |

(52) U.S. Cl.
CPC ......... *G01N 33/5032* (2013.01); *G01N 15/10* (2013.01); *G01N 27/447* (2013.01); *G01N 33/4915* (2013.01); *G01N 2015/1006* (2013.01)

(58) Field of Classification Search
CPC ............... G01N 33/5032; G01N 33/49; G01N 33/4915; G01N 27/447; G01N 15/10; G01N 2015/1006
See application file for complete search history.

(56) References Cited

U.S. PATENT DOCUMENTS

| | | | |
|---|---|---|---|
| 7,138,269 B2 | 11/2006 | Blankenstein | |
| 7,699,767 B2 | 4/2010 | Mueth et al. | |
| 2014/0200240 A1* | 7/2014 | Gabriel | G01N 33/49 514/301 |

FOREIGN PATENT DOCUMENTS

| | | |
|---|---|---|
| WO | 2004/109271 A1 | 12/2004 |
| WO | 2005/108627 A2 | 11/2005 |
| WO | 2007/008064 A2 | 1/2007 |
| WO | 2013/013228 A1 | 1/2013 |

* cited by examiner

*Primary Examiner* — J. Christopher Ball
(74) *Attorney, Agent, or Firm* — Collard & Roe, P.C.

(57) ABSTRACT

With a method for measurement of thrombocyte function, a solution is created, by which the sensitivity of individual thrombocytes can be measured with the least possible apparatus effort, with high throughput, by passing a liquid thrombocyte solution, in which the thrombocytes are present in isolated form, into a microfluidic chamber and brought into contact with at least one stimulant, wherein an electrical field directed transverse to the entry direction of the thrombocyte solution is applied to the chamber, and the movement path of the thrombocytes in the electrical field is observed and evaluated, in such a manner that thrombocytes having a movement path directed in the direction toward the minus pole of the electrical field are classified as non-activated thrombocytes, and thrombocytes having a movement path directed in the direction toward the plus pole of the electrical field are classified as activated thrombocytes.

8 Claims, 2 Drawing Sheets

METHOD FOR MEASUREMENT OF THROMBOCYTE FUNCTION

CROSS REFERENCE TO RELATED APPLICATIONS

Applicant claims priority under 35 U.S.C. §119 of German Application No. 10 2014 112 270.4 filed Aug. 27, 2014, the disclosure of which is incorporated by reference.

BACKGROUND OF THE INVENTION

1. Field of the Invention

The invention relates to a method for measurement of thrombocyte function.

2. Description of the Related Art

There is a need for thrombocyte function tests in the human and veterinary medicine sector, which tests can diagnose disorders of the thrombocytes (blood platelets) and of hemostasis, and can monitor anticoagulant therapies, in this connection that are more reliable in terms of prediction and more cost-effective, and can be used outside of clinical laboratories. The thrombocyte function tests that are currently available measure the reaction response of a thrombocyte population (several million thrombocytes) to agonists under static conditions. These conditions do not reflect in vivo conditions, where paracrine signals are dispersed, and also do not take into consideration the inherent differences in functional capacity (e.g. sensitivity) between different thrombocytes, particularly with regard to hypersensitive thrombocytes.

Light transmission aggregometry is considered the "gold standard" for thrombocyte function tests. Impedance aggregometry is not used extensively because of various factors that influence precision. At present, all thrombocyte tests analyze responses of a thrombocyte population to agonists (stimulants), but provide no information at the level of the individual thrombocytes.

A free-flow electrophoresis system having a microfluidic chamber is known from WO 2007/008064 A2, which system, as is sufficiently known for free-flow electrophoresis systems, serves to separate particles from one another on the basis of their electrical charges, and to analyze them, and to further influence the particles that have been separated in this manner, in a subsequent detection unit, if applicable.

A method is known from WO 2013/013228 A1, which primarily serves to study blood samples of patients to whom a medication was previously administered, in order to check the efficacy of the medication. Alternatively, it can also be provided to add such a medication or a corresponding substance directly to the blood sample, without previously administering it to the patients, and to conduct the corresponding tests afterward. Subsequently, in other words after the action of the medication or a corresponding substance on the blood sample, the sample is passed into an electrical field, and a distinction between activated and non-activated thrombocytes is made on the basis of the different deflection in the electrical field.

Microfluidic systems for characterization of particles and blood cells are known from U.S. Pat. No. 7,138,269 B2. In these systems, an electrical field can be used in order to characterize differently charged particles by means of different movement in the microfluidic system, wherein the individual particles can be examined individually. In this connection, a reagent can be added to the solution to be examined, which contains the particles, before the test.

SUMMARY OF THE INVENTION

It is the task of the invention to make a solution available, by means of which the sensitivity of individual thrombocytes can be measured with high throughput, with the least possible apparatus effort and expenditure.

This task is accomplished, in a method of the type indicated initially, according to the invention, in that a liquid thrombocyte solution, in which the thrombocytes are present in isolated form, is passed into a microfluidic chamber, to which an electrical field directed transverse to the entry direction of the thrombocyte solution is applied, and brought into contact with at least one stimulant directly before or during the action of the electrical field. The movement path of the thrombocytes in the electrical field is observed and evaluated in such a manner that thrombocytes having a movement path directed in the direction toward the minus pole of the electrical field are classified as activated thrombocytes, and thrombocytes having a movement path directed in the direction toward the plus pole of the electrical field are classified as non-activated thrombocytes.

With the invention, a method is made available, with which it is possible, with little apparatus effort, to measure the sensitivity of individual thrombocytes, with high throughput. For this purpose, a thrombocyte solution, in which the thrombocytes are present in isolated manner, in other words a greatly diluted thrombocyte solution, for example, is brought together with a stimulant that acts on the thrombocytes, directly before or during the effect of an electrical field. Depending on the efficacy of the stimulant (of the agonist), the surface of the individual thrombocyte changes in known manner, and its electrical charge state changes accordingly. It is known that the surface charge of a non-activated thrombocyte is negative and that the surface charge of an activated thrombocyte is less negative to positive. Depending on whether or not activation of the respective thrombocyte by the stimulant has taken place (when using an activator as a stimulant), the movement path of the individual thrombocyte in the electrical field changes; this path can be observed microscopically, in simple manner. Likewise, when using an inhibitor as a stimulant, the efficacy of the inhibitor on the respective thrombocyte can be checked by means of observation of the movement path of the thrombocyte. Depending on the progression of the movement path, classification of the thrombocyte is then possible in simple manner. The electrical field in the microfluidic chamber is therefore not used for (particle) separation, but rather the change in the movement paths is evaluated, and mixing of the particles (thrombocytes) with a stimulant, directly before or during the action of the electrical field, takes place.

In a particularly preferred embodiment, it is provided that the thrombocyte solution is first brought into contact with a first stimulant, and subsequently, downstream, is brought into contact with a second stimulant in the chamber. The first stimulant is then preferably an activator, and the second is an inhibitor.

In a preferred further embodiment, the liquid thrombocyte solution may be passed into a microfluidic free-flow electrophoresis chamber.

Combining or mixing the thrombocyte solution with the stimulant can take place in different ways.

According to a first embodiment, it is provided that the liquid thrombocyte solution is first combined with a stimulant solution, and subsequently the mixed thrombocyte/stimulant solution is passed into the microfluidic chamber. Mixing therefore takes place, in this embodiment, directly before introduction into the microfluidic chamber.

According to a second embodiment, it is provided that the liquid thrombocyte solution and a stimulant solution are passed into the microfluidic chamber in parallel. Mixing then takes place only in the region of action of the electrical field.

Finally, it is provided, as an alternative, that before introduction of the thrombocyte solution into the microfluidic chamber, stimulant particles are immobilized at the bottom of the chamber. The thrombocyte solution and thereby the thrombocytes then come into contact with the stimulant particles that are disposed in the chamber in stationary manner. Immobilization at the bottom of the chamber is also particularly well suited for bringing the thrombocytes into contact with a second stimulant.

In the sense of the invention, a stimulant solution should be understood to mean not only solutions as such, but also suspensions in which non-dissolved stimulant particles are present.

Fundamentally, all stimulants known and suitable for thrombocyte treatment can be used; preferably, adenosine diphosphate, collagen, thrombin or prostaglandin is used as an activator, and acetylsalicylic acid, convulxin, clopidogrel, prasugrel, ticagrelor, or prostacyclin is used as an inhibitor.

A Hepes buffer, for example, can be used as a fluid carrier medium for the thrombocytes in the thrombocyte solution.

According to a first embodiment, it can preferably be provided, for evaluation of the movement path of the thrombocytes, that the movement path of the thrombocytes in the chamber is imaged by means of imaging methods or optical detection methods.

The electrical field in the microfluidic chamber can be generated by direct voltage or by pulsed direct voltage. The electrodes for generating the electrical field can be disposed in the microfluidic chamber. They can be micro-fabricated electrodes or wire electrodes. The electrodes consist, for example, of gold, platinum, graphite or other conductive material that can be imprinted onto a transparent substrate, such as glass or polymethylmethacrylate, or they are produced from these materials, in wire form.

The electrodes are separate from the actual flow channel, within the microfluidic chamber, by a boundary zone (e.g. electrolyte bridges), which zone can be formed from a polymer matrix such as a hydrogel or a similar material, or which is embodied by a series of micro-channels.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF PREFERRED EMBODIMENTS

Figure 1:
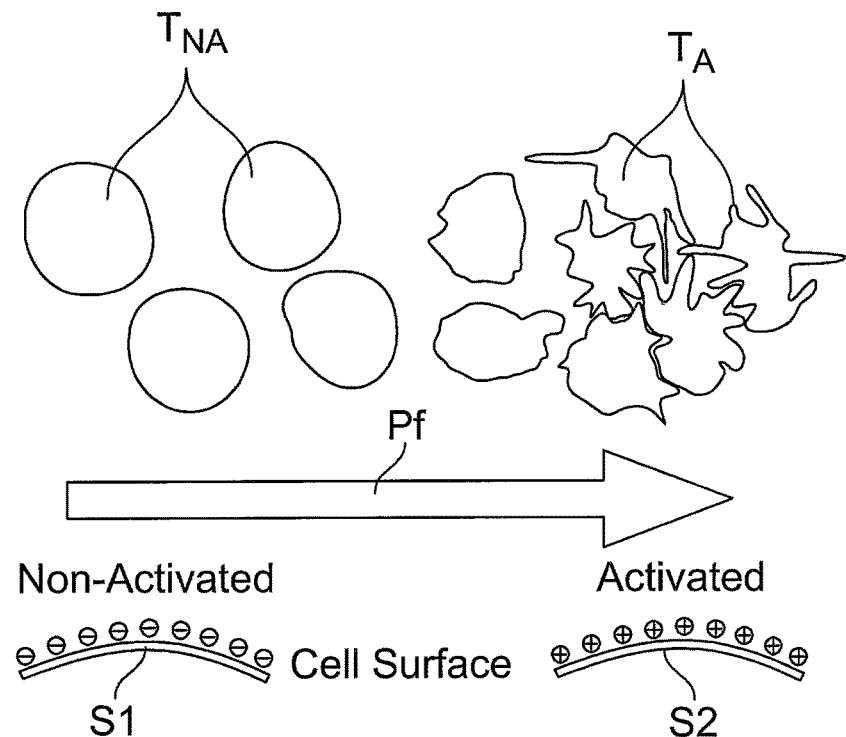
FIG. 1 is a schematic representation of the fundamental surface structure of non-activated and activated thrombocytes.

In FIG. 1, non-activated thrombocytes, configured in round manner, are indicated with $T_{NA}$, on a greatly enlarged scale. These non-activated thrombocytes $T_{NA}$ have a negative surface charge at their surface S1.

If these non-activated thrombocytes $T_{NA}$ are activated by a stimulant or an agonist, as indicated by the arrow Pf, the activated thrombocytes $T_A$ assume a different, namely an irregular surface, structure and membrane components arrange themselves differently in the thrombocyte membrane, so that the electrical charge at the surface S2 of the activated thrombocytes $T_A$ is less negative to positive. The method according to the invention makes use of this different surface charge distribution of non-activated thrombocytes $T_{NA}$ and of activated thrombocytes $T_A$.

Figure 2:
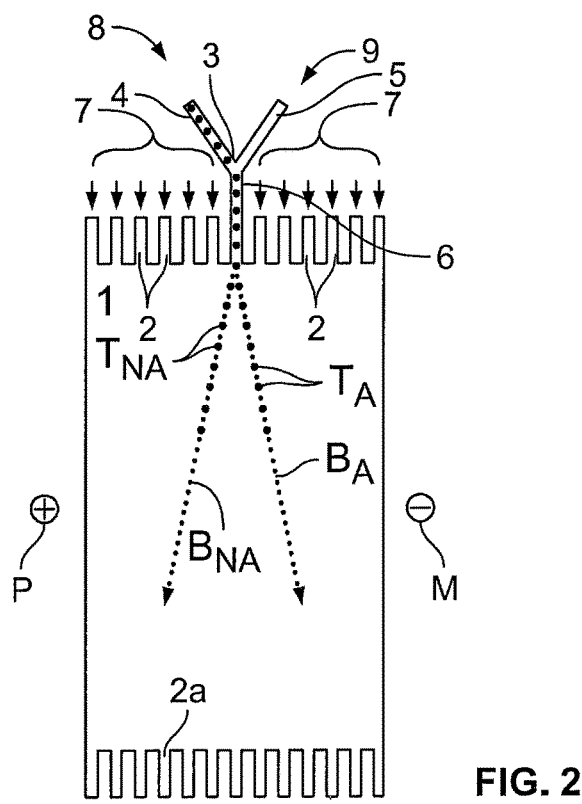
FIG. 2 is a top view of a free-flow electrophoresis chamber with a first embodiment of the thrombocyte feed.

In FIG. 2, a microfluidic chamber in the form of a free-flow electrophoresis chamber 1 is shown, to which an electrical field is applied transverse to the main flow direction, which extends in the longitudinal direction of the chamber 1, which field is indicated with a plus pole P and a minus pole M. Suitable electrodes are disposed in the edge regions of the chamber 1, on both sides, accordingly, or are integrated into the chamber 1, if the electrodes are imprinted electrodes.

The free-flow electrophoresis chamber 1 has a plurality of parallel entry channels 2 and exit channels 2a. In the exemplary embodiment according to FIG. 2, a Y-shaped feed line 3 is connected to a central entry channel, through the one inflow 4 of which a thrombocyte solution 8 with individual non-activated thrombocytes $T_{NA}$ is fed in, and through the other inflow 5 of which a stimulant solution 9 is fed in; these solutions mix in a mixing region 6 of the feed line 3, and get into the chamber 1 in mixed form. Parallel to this entry, a running buffer 7 is passed into the chamber 1 through the further channels 2, so that flow through the chamber 1 takes place over its entire width and length.

The thrombocyte solution 8 preferably consists of a Hepes buffer, aside from the non-activated thrombocytes $T_{NA}$ contained in the solution in isolated manner; the running buffer 7 can also be a Hepes buffer, but can also be a stimulant solution, if applicable.

In the mixing region 6 of the Y-shaped feed line 3, the stimulant solution 9 acts on the thrombocytes, thereby causing some thrombocytes to be activated and their surface charge to change from negative to less negative to positive. As a result, the movement path $B_{NA}$ of the non-activated thrombocytes $T_{NA}$ extends in the direction of the plus pole P in the influence region of the electrical field, within the chamber 1, while the movement path $B_A$ of the activated thrombocytes $T_A$ extends in the direction of the minus pole M.

According to the invention, the respective movement path of each individual thrombocyte is detected, for example by means of a microscope; thrombocytes with a movement path directed toward the plus pole are classified and evaluated (in other words qualified) as non-activated thrombocytes $T_{NA}$, and thrombocytes with a movement path $B_A$ directed toward the minus pole as activated thrombocytes $T_A$.

Figure 3:
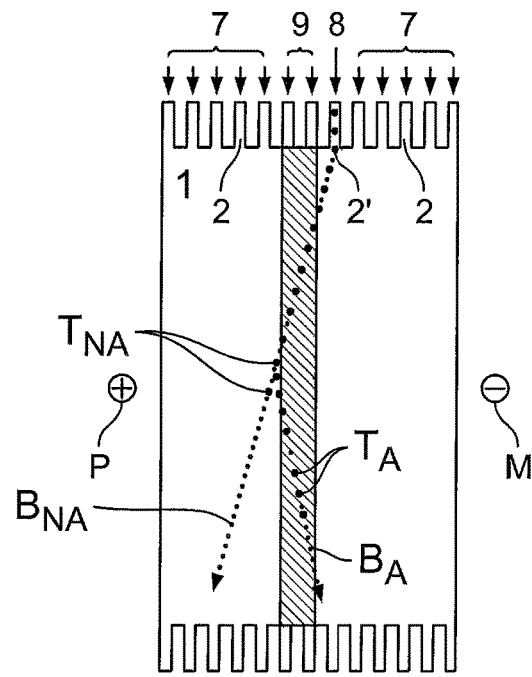
FIG. 3 shows a free-flow electrophoresis chamber in a top view, with a second embodiment of the feed to the solution.

In the exemplary embodiment according to FIG. 3, the feed of the thrombocyte solution 8 and of the stimulant solution 9 into the chamber 1 is different, as compared with the exemplary embodiment according to FIG. 2; for the remainder, the exemplary embodiment does not differ from the exemplary embodiment according to FIG. 2. In the exemplary embodiment according to FIG. 3, the stimulant solution 9 is centrally introduced into the inlet channels 2, and flows through the chamber 1 essentially along the cross-hatched region. The thrombocyte solution 8 is introduced through an entry channel 2' disposed adjacent thereto. By means of the action of the electrical field in the chamber 1, the thrombocytes $T_{NA}$ that are at first not activated are deflected in the direction of the plus pole, and thereby come into contact with the stimulant solution 9. Those thrombocytes that remain non-activated, in other words the thrombocytes $T_{NA}$, move along a movement path shown as $B_{NA}$, in the direction of the plus pole P. In contrast, thrombocytes $T_A$ that have been activated by coming into contact with the stimulant solution change their movement path; ultimately, their movement path $B_A$ is directed in the direction of the minus pole M. Therefore, these thrombocytes can be classified in this exemplary embodiment, as well, by observation of the movement path $B_{NA}$, $B_A$ of the individual thrombocytes; thrombocytes with a movement path $B_{NA}$ that is ultimately directed toward the plus pole P are non-activated thrombocytes $T_{NA}$, and thrombocytes with a movement path $B_A$ that is ultimately directed toward the minus pole are activated thrombocytes $T_A$.

Figure 4:
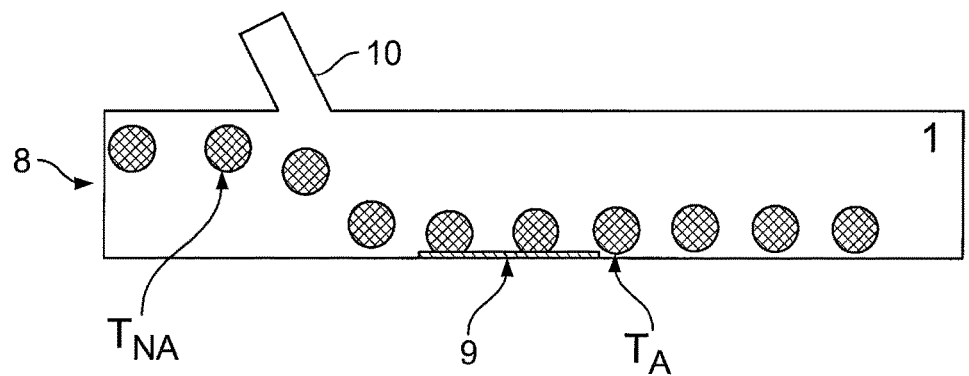
FIG. 4 shows a free-flow electrophoresis chamber in a side view, with a third embodiment of the thrombocyte feed.

In FIG. 4, a further embodiment is shown; the free-flow electrophoresis chamber 1 is rotated by 90° as compared with the representation according to FIGS. 2 and 3, and shown from the side. In this embodiment, no stimulant solution is introduced into the chamber; instead, stimulant particles are immobilized on the bottom surface of the chamber 1.

The thrombocyte solution 8 is fed in through the inlet channels 2, just like a separation buffer, which is not shown in FIG. 4. In addition, an additional buffer for dynamic focusing is introduced into the chamber 1 through an inlet 10 on the top side.

Thrombocytes that are activated are once again shown with $T_A$; their movement path is then deflected transverse to the plane of the drawing of FIG. 4, in the direction of the minus pole. The evaluation of the movement paths of the individual thrombocytes in the chamber 1 takes place as described above.

Of course, the invention is not restricted to the exemplary embodiments shown. Further embodiments are possible without departing from the fundamental idea. For example, the thrombocyte solution can first be brought into contact with a first stimulant, and subsequently, downstream, into contact with a second stimulant, in the chamber. The first stimulant is then an activator, for example, and can be brought into contact with the individual thrombocytes in the manner described in FIGS. 2 to 4. The second stimulant is then an inhibitor, for example, which is immobilized on the bottom of the chamber 1, preferably downstream from the entry into the chamber 1, or is introduced into the chamber 1 downstream from the entry into the chamber 1. The movement path of the thrombocytes in the entry region of the chamber 1 then reflects the efficacy of the activator on the thrombocytes and the movement path of the thrombocytes downstream reflects the efficacy of the inhibitor on the thrombocytes.

Although only a few embodiments of the present invention have been shown and described, it is to be understood that many changes and modifications may be made thereunto without departing from the spirit and scope of the invention.

What is claimed is:

1. A method for measurement of thrombocyte function comprising
   (a) passing a liquid thrombocyte solution comprising thrombocytes in isolated form into a microfluidic chamber;
   (b) applying to the microfluidic chamber an electrical field directed transverse to an entry direction of the thrombocyte solution;
   (c) first bringing the thrombocyte solution into contact with a first stimulant directly before or during action of the electrical field;
   (d) subsequently, downstream, bringing the thrombocyte solution into contact with a second stimulant in the microfluidic chamber; and
   (e) observing and evaluating a respective movement path of each individual thrombocyte in the electrical field so that a thrombocyte having a movement path directed toward a minus pole of the electrical field is classified as an activated thrombocyte and a thrombocyte having a movement path directed toward a plus pole of the electrical field is classified as a non-activated thrombocyte.

2. The method according to claim 1, wherein the microfluidic chamber is a microfluidic free-flow electrophoresis chamber.

3. The method according to claim 1, wherein the liquid thrombocyte solution is first brought together with a stimulant solution containing the first stimulant to form a mixed thrombocyte/stimulant solution, and subsequently the mixed thrombocyte/stimulant solution is passed into the microfluidic chamber.

4. A method for measurement of thrombocyte function comprising
   (a) passing a liquid thrombocyte solution comprising thrombocytes in isolated form into a microfluidic chamber;
   (b) applying to the microfluidic chamber an electrical field directed transverse to an entry direction of the thrombocyte solution;
   (c) bringing the thrombocyte solution into contact with at least one stimulant directly before or during action of the electrical field; and
   (d) observing and evaluating a respective movement path of each individual thrombocyte in the electrical field so that a thrombocyte having a movement path directed toward a minus pole of the electrical field is classified as an activated thrombocyte and a thrombocyte having a movement path directed toward a plus pole of the electrical field is classified as a non-activated thrombocyte; and
   (e) wherein the liquid thrombocyte solution and a stimulant solution containing the at least one stimulant are passed into the microfluidic chamber in parallel.

5. A method for measurement of thrombocyte function comprising
   (a) passing a liquid thrombocyte solution comprising thrombocytes in isolated form into a microfluidic chamber;
   (b) applying to the microfluidic chamber an electrical field directed transverse to an entry direction of the thrombocyte solution;
   (c) bringing the thrombocyte solution into contact with at least one stimulant directly before or during action of the electrical field; and
   (d) observing and evaluating a respective movement path of each individual thrombocyte in the electrical field so that a thrombocyte having a movement path directed toward a minus pole of the electrical field is classified as an activated thrombocyte and a thrombocyte having a movement path directed toward a plus pole of the electrical field is classified as a non-activated thrombocyte; and (e) wherein before introduction of the thrombocyte solution into the microfluidic chamber, stimulant particles of the at least one stimulant are immobilized on the bottom of the chamber.

6. The method according to claim 1, wherein the first stimulant comprises an activator selected from the group consisting of adenosine diphosphate, collagen, thrombin and prostaglandin.

7. The method according to claim 1, wherein the second stimulant comprises an inhibitor selected from the group consisting of acetylsalicylic acid, convulxin, clopidogrel, prasugrel, ticagrelor, and prostacyclin.

8. The method according to claim 1, wherein the movement path of the thrombocytes in the chamber is imaged using an imaging method or an optical detection method.

* * * * *